United States Patent [19]

Molday

[11] Patent Number: 4,744,760
[45] Date of Patent: May 17, 1988

[54] COLLOIDAL SIZED METAL-POLYSACCHARIDE PARTICLES

[75] Inventor: Robert S. Molday, Vancouver, Canada

[73] Assignee: University of British Columbia, Vancouver, Canada

[21] Appl. No.: 691,508

[22] Filed: Jan. 14, 1985

[30] Foreign Application Priority Data

Apr. 24, 1984 [CA] Canada ................................. 452605

[51] Int. Cl.$^4$ ....................... G01N 1/00; G01N 25/00; G01N 31/00
[52] U.S. Cl. ........................................ 424/3; 424/132; 424/147; 424/493; 514/6; 514/59; 128/653; 536/51
[58] Field of Search ..................... 424/3, 35, 132, 147; 128/653; 514/6, 59; 536/51

Primary Examiner—Frederick E. Waddell
Attorney, Agent, or Firm—Spensley Horn Jubas & Lubitz

[57] ABSTRACT

Colloidal sized particles comprising metal particle coated with a water soluble polysaccharide derivative. The derivative is such that when it is not coating the metal, it has at least one, and preferably a number, of pendant functional groups each of which has a positive charge in aqueous solution. The metal is preferably selected from the group consisting of gold, platinum, and silver, whereas the polysaccharide may usefully be selected from the group consisting of dextran and mannan. The particles can be used as markers for biologically active molecules, or for separating different types of such molecules.

22 Claims, 3 Drawing Sheets

COLLOIDAL SIZED METAL-POLYSACCHARIDE PARTICLES

FIELD OF THE INVENTION

This invention relates to colloidal sized particles comprising a metal particle coated with a polysaccharide derivative, which particles are useful in labelling biologically active molecules and for assisting in separating various types of such molecules.

DESCRIPTION OF PRIOR ART

For ultrastructural investigation of biologically active substances, macromolecular markers must satisfy two main requirements. They must be visible in biological specimens under the Transmission Electron Microscope (TEM) or Scanning Electron Microscope (SEM), and in addition must be suitable for use with specific labelling methods. To be visible in thin section, TEM markers must be sufficiently electron dense for contrast from stained subcellular structures. For imaging under SEM and replica methods for TEM, macromolecular markers must have a characteristic size and shape which enable them to be recognized on cell surfaces or other biological structures. Furthermore, such markers should have surface properties such that they will not aggregate in physiological buffer, should have a low degree of adsorption to cell surfaces and subcellular structures, and tightly bind to specific ligands.

TABLE I
Macromolecular Markers for EM

| MARKER | SHAPE/SIZE (nm) | PRINCIPLE MODE OF DETECTION USES | REFERENCES |
| --- | --- | --- | --- |
| Ferritin | Spherical 12-15 | SEM- secondary electrons TEM- thin sections | Tokunaga et al., IITRI Scanning Electron Microsc. (1976) I, 301-310. |
| Hemocyanin | Cylindrical 35 (diameter) × 50 (length) | SEM- secondary electrons TEM- replica methods/thin sections | Weller, J. Cell Biol. (1974) 63, 699-707. Rosenberg et al., Gonda, J. Histochem. Cytochem. (1979a, b) 27, 1445-1454. |
| Viruses | | | |
| Tobacco mosaic virus | Rod 15-300 | SEM- secondary electrons TEM- thin sections | Hammerling et al., J. Exp. Med. (1975) 141, 515-523. |
| Bushy stunt virus | Spherical 30 | | Nemanic et al., J. Cell Biol. (1975) 64, 311-21. |
| Bacteriophage T-4 | 220 head-tail 85-115 hexagonal head | SEM- secondary electrons | Kumon, Virology (1976) 74, 93-103. |
| Peroxidase reaction product | Irregular particles or crystals | SEM- secondary electrons TEM- thin sections | Bretton et al., J. Microscopy (1973) 17, 93-96. McKeever et al., J. Histochem. Cytochem. (1977) 25, 1063-1068. |
| Copolymer microspheres | spherical 30-340 | SEM- secondary electrons fluorescent microscopy | Molday et al., J. Immunol. Meth. (1982) 52, 353-367. |
| Polystyrene latex spheres | Spherical 200-1000 | SEM- secondary electrons | Lo Buglio et al., IITRI/Scanning Electron Microscopy. (1972) 313-320. Linthicum, J. Ultrastruc. Res. (1975) 51, 55-68. |
| Silica Spheres | Spherical 7-25 | SEM- secondary electrons TEM- replica methods | Peters et al., IITRI Scanning Electron Microsc. (1976) II 75-84. |
| Iron copolymer microspheres | Spherical 30-50 | SEM- secondary electrons and X-ray | Molday et al., Nature (1977) 268, 437-438. |
| Iron dextran microspheres | Spherical 20-40 | SEM- secondary electrons TEM- thin sections | Molday et al., J. Immunol. Meth. 52 (1982), 353-367. Baccetti et al., J. Microsc. (1977) 109, 203-209. Dutton et al., Proc. Natl. Acad. Sci. U.S.A. (1979) 76 3392. |
| Gold particles | Spherical or oblong 5-160 | SEM- secondary electrons, backscatter electrons, X-ray | Horisberger et al., Experientia 31 (1975), 1147-1149; J. Histochem Cytochem. (1977) 25, 295-305; Experientia 34 (1978) 274-76; J. Microsc. 115, (1979) 97-102; Scanning Electron Microsc. II (1981) 9-32. |

A large number of markers which satisfy at least some of the foregoing requirements to some degree, have been used in the past. The most common of such markers are listed in Table I.

Of particular interest as markers are the heavy metal complexes or colloids, such as Ferritin (which consists of a ferric oxide core approximately 7 nm in diameter surrounded by protein composed of 24 identical subunits), iron dextran particles (such as those mention in Table I, as well as those described by Martin and Spier in J. Histochem. Cytochem. (1974) 22,206-207), and colloidal gold. The iron dextran particles are particularly useful in that periodate-borohydride reactions can be used to chemically bond proteins to the dextran for use in labelling studies, as described by Dutton et al, op. cit.

One of most useful TEM and SEM markers is colloidal gold. Such particles can be synthesized in a range of sizes from 5 nm to 160 nm by reduction of chloroauric acid with a variety of reducing agents, as described by Frens, Nature 241,20–22, and Horisberger, *Scanning Electron Microsc.* (1981) II, 9–32. Such particles are highly electron dense and therefore they can readily be seen in thin sections against even heavily stained subcellular material under the TEM. Under the SEM, gold particles produce a high emission of electrons which can be detected by either secondary or backscatter imaging. Thus, on uncoated or lightly coated specimens, the gold particles often appear as bright spots and can be readily distinguished from other particles on cell surfaces. Furthermore, gold particles also emit characteristic X-rays which can be detected with an appropriate X-ray detector. However, although these particles have optimal properties for detection by EM they have some limitations in their interaction with ligands. Proteins such as antibodies and lectins must be adsorbed to the surface of the gold rather than covalently bonded. This interaction varies with the physical properties of the protein and the ionic strength and pH of the buffer (Goodman et al., *Scanning Electron Microsc.* (1979) III 619–626). Thus, conditions have to be regulated to enable proteins to bind to the gold particles without inducing aggregation of the particles. This has been successfully achieved for Protein A, immunoglobulins, Con A and a variety of other ligands (Horisberger, *Scanning Electron Microsc.* (1981) II 9–32). Some ligands, however, such as wheat germ agglutinin (WGA) and lentil lectin do not form stable conjugates with gold particles. Furthermore, the proteins adsorbed to gold have been reported to disassociate even under mild conditions (Goodman et al., *Scanning Electron Microsc.* (1979) III 619–626), and the number of ligands bound per gold cannot be easily regulated.

Some degree of stabilization of gold has previously been obtained by Bontoux et al., *J. Chim. Phys. Physicochim. Biol.* (1969) 66, 1259–1263. However, little stabilization of gold by dextran was described in the foregoing paper, except where the dextran had a molecular weight of about 100,000 or greater. Some stabilization was observed with dextran greater than 100,000, which is hypothesized to be due to viscosity effects.

It is desirable then to have particles which have the same advantages as the colloidal gold particles described above, but which can be linked to a large number of biologically active molecules, i.e. bonded to them either directly or indirectly as for example through suitable ligands, and which particles are stable in aqueous solution, particularly saline solutions.

SUMMARY OF THE INVENTION

The present invention provides particles which are of colloidal size, with each of such particles comprising a metal particle of a type which exhibits thereon a charge in aqueous suspension (typically a negative charge), coated with a water soluble polysaccharide derivative. The derivative is selected such that when it is not coating the metal, it has at least one and preferably more, pendant functional groups each of which has a charge thereon (typically positive) in aqueous solution opposite to that on the metal particles. The metal is preferably selected from the group consisting of gold, platinum, and silver, with gold being particularly preferred. The pendant functional groups previously described preferably each contain a nitrogen atom which is positively charged in aqueous solution. Further, the polysaccharide derivative is preferably obtained from a compound having two nitrogen atoms, each of which has a positive charge in aqueous solution. Such compounds are typically arginine, histidine, and a diaminoalkane, such as diaminoethane, diaminopentane or diaminohexane.

The polysaccharide is usefully from the group consisting of dextran and mannan. Furthermore, the particles described, are typically of a size of about 2 to 200 nm, and the polysaccharide typically has a molecular weight of between about 5000 to 70,000.

A method of making such particles, and a method for separating different types of biologically active molecules (that is complex organic molecules normally found in biological system, such as lectins, antibodies, proteins, antigens on cells, etc.) based upon linkage of the particles described to one type of molecule in a mixture, followed by separations based upon difference in density, are also provided.

DESCRIPTION OF DRAWINGS

The use of embodiments of the invention will be described, with reference to the drawings, which are electron micrographs as follows.

DETAILED DESCRIPTION OF EMBODIMENTS OF THE INVENTION

Preparation Of Metal-Dextran Particles

Figure 1:
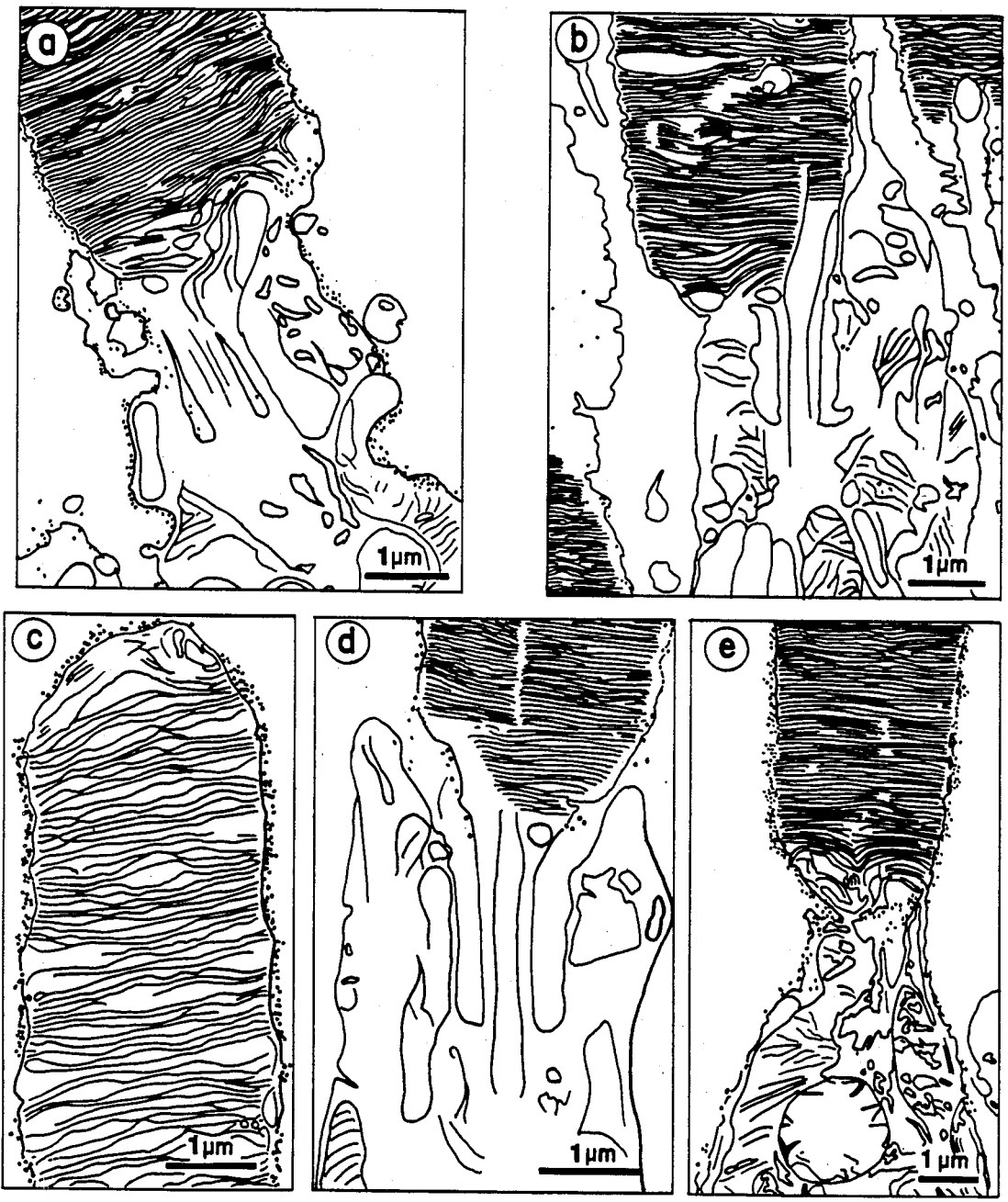
FIG. 1 Lectin receptors on pre-fixed rod photoreceptor cells in bovine retina labelled with dextran-gold. (a) Cell treated with Con A, 24 hours at 4 C, followed by Au-DE-Dex (approx. 30 nm in diameter) prepared as later described, 24 hours at 4 C. Notice intense labelling along both outer and inner segments. (b) Control cell treated with Con A in the presence of 0.1M α-methyl-mannoside followed by Au-DE-Dex (approx. 30 nm diameter) as in (a); (c) Outer segment directly labelled with WGA-DE-Au-Dex (approx. 40 nm diameter), 4 hrs at 4 C. (d) Same conditions as (c), showing absence of label on inner segment. (e) Cell incubated with smaller WGA-Au-Dex (approx. 17 nm diameter) conjugate for 4 hrs at 4 C. Notice sparse label present on inner segment (arrowhead).

Gold particles of various sizes from 17 nm to 60 nm were prepared by reduction of choloroauric acid with sodium citrate as described by Frens (Nature (1973) 241, 20-22) and Horisberger (J. Microsc. (1979), 115, 97-102). Diaminoethane-derivatized Dextran T-10 (Pharmacia) (T-10 indicating an average molecular weight of 10,000) was prepared by reacting a solution of 10 gms of dextran in 50 ml of 0.1M sodium acetate (pH 5), with 1.6 gms of sodium periodate for 1.5 hours. It will be understood that all solutions and suspensions mentioned throughout this application are aqueous, unless indicated otherwise. The dextran solution was dialyzed against 6 l. of water and then reacted with 0.5M diaminoethane at pH 9.5. After 1 hour 0.72 gms of the reducing agent sodium borohydride was added to stabilize the diaminoethane-derivatized dextran (DE-Dex). Finally the solution was exhaustively dialyzed and lyophilized. DE-Dex-Au particles were prepared by adding 100 mg of DE-Dex to 100 ml of Au in 2 mM phosphate buffer, pH 7.

Diaminoethane-derivatives of dextran, in one case having an average molecular weight of 10,000 and in the other case an average molecular weight of 40,000, were also prepared without first oxidizing the dextran. First, 5 g of the dextran were dissolved in 15 ml 2M aqueous diaminoethane. The pH was adjusted to 10.8 with acetic acid. The solution was stirred at room temperature overnight, with the resultant product being stabilized with $NaBH_4$. The resulting solution was extensively lyophilized. Prior to proceeding, the resultant product at a concentration of 1 mg/ml $H_2O$ was tested for free amino groups with trinitrobenzene sulfonic acid. This test was strongly positive, although removal of all free diaminoethane was confirmed by gel filtration chromatography. Thus, bonding of one amino group only of the diaminoethane to dextran, was confirmed. Colloidal gold was produced by the method described above, by reacting 4 ml 1% sodium citrate, 100 ml boiling $H_2O$, and 0.1 ml 10% $AuCl_4$. The diaminoethane-dextran was then added to the colloidal gold to produce diaminoethane-dextran gold particles.

For comparison, other gold-dextran particles were prepared as summarized in Table II described below, but wherein underivatized dextran was utilized.

Platinum-dextran particles and silver-dextran particles were prepared in a manner analogous to preparation of the gold-dextran particles described above. The required platinum suspension was obtained by reacting 100 ml boiling $H_2O$, 5 ml 1% aqueous sodium citrate, and 0.2 ml aqueous 10% platinum chloride. The resulting colloid appeared stable, but upon adding an equal volume of 10% NaCl, the colloid aggregated. A silver suspension for preparation of silver-dextran particles was likewise prepared withe 100 ml boiling $H_2O$, 10 ml 1% aqueous sodium citrate, and 0.2 ml aqueous silver nitrate. The resulting mixture turned milky brown within 30 minutes. The remainder of the steps for preparation of the dextran derivatives listed in Table II, were again analogous to that described above for gold.

Dextran was in some cases replaced with a crosslinked polymer of sucrose having an average molecular weight of 70,000 and sold under the trade mark FICOLL 70, as well as replaced with polyethylene glycol having a molecular weight of 20,000 sold under the trade mark Carbowax or mannan, to produce those particles as noted Table II. Furthermore, in many cases diaminoethane was replaced with another diaminoalkane, in particular diaminopentane and diaminohexane.

Stability

The stability of the suspensions of various particles produced, was tested by adding 0.2 ml 10% NaCl of the suspenion in each case (except as noted in Table II). The results are summarized in Table II. It should be noted that the formulae used in that table and throughout this application are not structural formulae and are not intended to show the actual bonding arrangements between molecules. In each case wherever the metal particle was coated with the diaminoethane-derivative of a polysaccharide in particular a polyhexose, (ie, dextran or mannan), whether oxidized or not, the suspension was stable for any of the three metals tested, but was otherwise unstable. It is preferred though that the dextran used is first oxidized with periodate, since this produces a higher concentration of diaminoethane linked to the dextran, and hence should result in greater stability of the metal-diaminoethane-dextran particles.

TABLE II

Stability of Various Suspensions

| No. | Particle | Stability (0.8 ml of suspension + 0.2 ml 10% NaCl) |
|---|---|---|
| 1. | Dex(T-10)-Au | agg. |
| 2. | Dex(T-40)-Au | agg. |
| 3. | DE-OxDex(T-10)-Au | stable |
| 4. | DE-Dex(T-10)-Au | stable |
| 5. | DE-Dex(T-40)-Au | stable |
| 6. | DE-OxMann-Au | stable |
| 7. | Dex(T-5)-Pt | floc |
| 8. | OxDex(T-5)-Pt | floc |
| 9. | Dex(T-10)-Pt | floc |
| 10. | Dex(T-40)-Pt | floc |
| 11. | DE-Dex(T-10)-Pt | stable |
| 12. | Ficoll70-Pt | floc |
| 13. | Carbowax-Pt | floc |
| 14. | $H_2O$—Pt | floc |
| 15. | Dex(T-5)-Ag | floc |
| 16. | OxDex(T-5)-Ag | floc |
| 17. | Dex(T-10)-Ag | floc |
| 18. | Dex(T-40)-Ag | floc |
| 19. | DE-Dex(T-10)-Ag | stable |
| 20. | Ficoll70-Ag | floc |
| 21. | $H_2O$—Ag | floc |

Notes
agg. - aggregates
Dex - Dextran
OxDex - oxidized dextran
DE - diaminoethane derivative
(T- ) - average molecular weight
*- 1.0 ml of suspension used In addition, the replacement of diaminoethane by the diaminoalkane, namely diaminopentane or diaminohexane, as mentioned above, did not appear to effect stability of the suspensions (although these results are not summarized in Table II).

Preparation Of Metal-Dextran Particles Using Other Dextran Derivatives

It appeared that the positively charged pendant amino groups in the aqueous suspension, stabilized the metal particles which are known to be negatively charged in an aqueous solution. This stabilization of the metal by a polysaccharide derivative having pendant functional groups positively charged in aqueous solution, was confirmed by preparation of similar particles wherein the polysaccharide derivative was produced by reacting arginine or histidine with periodate oxidized dextran (average molecular weight 10,000). The procedure was analogous to that first described above, the arginine or distidine in effect replacing the diaminoethane. 5 ml of periodate oxidized dextran as described, was reacted with 5 ml of a saturated aqueous solution of arginine or histidine for a period of 2 hours, with the pH being maintained at about 8–8.5. The resulting product was dialyzed extensively, and in each case was added to a 0.5 ml gold colloid followed by addition of 0.2 ml 10% NaCl. In both cases, no precipitate resulted, thereby again confirming stabilization of the negatively charged metal particle by the polysaccharide derivative having positively charged pendant functional groups in the aqueous solution.

Preparation of Glutaraldehyde Activated Dextran Coated Gold Particles

For preparation of these particles, 100 mgs of DE-Dex (prepared from oxidized dextran, as is all of the dextran derivatives described in the remainder of this Disclosure) in 4.5 ml 2 mM sodium phosphate buffer was reacted with 0.5 ml of 25% aqueous glutaraldehyde. Alternatively, DE-Dex (100 mg) can be added to 100 ml of freshly prepared colloidal gold, followed by addition of 2 ml of glutaraldehyde. After 10 min the dextran solution was added with stirring to 100 ml of colloidal gold. The mixture was stirred for several hours and the gold was then washed twice with 0.02M phosphate buffer by centrifugation at 15,000 rpm for 40 min. in a Sorvall SS-34 rotor. The final pellet was resuspended in 3 ml of 0.02M phosphate and reacted with protein (WGA, avidin, ovomucoid, Protein A or antibody) at a final concentration of 1–2 mg/ml. The reaction was allowed to proceed overnight (approximately 14 hours) and stopped by the addition of Tris buffered saline (TBS) containing 0.05M glycine. The conjugate was washed twice with 10 ml of TBS and the final pellet was resuspended in TBS containing 1 mg/ml bovine serum albumin (BSA) and 10 mM $NaN_3$ (to act as a bactericide).

Gold-dextran particles prepared either with diaminoethane derivatized dextran (DE-dextran) or glutaraldehyde-activated DE-dextran were stable in aqueous solution even under conditions of high salt in which uncoated gold particles precipitate (Horisberger, *J. Microsc.* (1979) 115, 97–102; Goodman et al., *Scanning Electron Microsc.* (1979) III, 619–626).

Application of Dextran-Gold Markers in Cell Labelling

Colloidal gold particles coated with dextran can be used as EM markers with a variety of direct and indirect labelling methods. Since dextran binds to Con A, Au-Dex markers can used to indirectly label Con A receptors on cell surfaces by linking thereto through Con A. FIG. 1a illustrates the labelling of Con A receptors on rod photoreceptor cells in bovine retina tissue. When the fixed tissue was treated with free Con A overnight, washed and subsequently labelled with Au-Dex particles overnight, a dense pattern of labelling could be seen on the inner and outer segments of the rod photoreceptor cell. When the Con A inhibitor α-methyl mannoside (0.1M) was included in the first labelling step, no labelling with gold-dextran could be visualized (FIG. 1b).

Markers consisting of gold-dextran conjugated to WGA wheat germ agglutimin (WGA) were used to directly label cells (ie. the gold-dextran particles were "linked" to biologically active molecules on the cells through WGA). Since (WGA) cannot be stably adsorbed to gold particles, it was reacted with glutaraldehyde-activated DE-Dex-Au particles. Stable conjugates were formed which agglutinated human red blood cells and specifically labelled a variety of cells including thymocytes, Chinese hamster ovary (CHO) cells, neuroblastoma cells, and terminal photoreceptor cells. Labelling could be visualized by the red appearance of the cells after treatment with WGA-DE-Dex-markers. This is in contrast to control cells which did not show a red colour after treatment with the same reagent in the presence of 0.01M N-acetyl chitobiose inhibitor. Labelling was verified by SEM and TEM analysis. WGA-DE-Dex-Au markers showed no appreciable loss in activity or tendency to aggregate when stored in TBS-BSA solution for several months.

When bovine retina tissue was labelled for 4 hours with WGA-Au-DE-Dex conjugates (approximate diameter 40 nm) a dense pattern of labelling was observed along the rod outer segment (FIG. 1c). However, no labelling was present on the connecting cilium and inner segment (FIG. 1d). Smaller makers (17 nm) (FIG. 1e), longer labelling times (24 hours), or indirect labelling techniques using free WGA followed by ovomucoid-Au-DE-Dex (not shown), all resulted in some labelling in this region although with a lower density than observed on the outer segment. This difference in labelling can be a result of differences in the number and/or accessibility of these lectin receptors on the outer and inner segment for WGA-Au-Dex markers.

Figure 2:
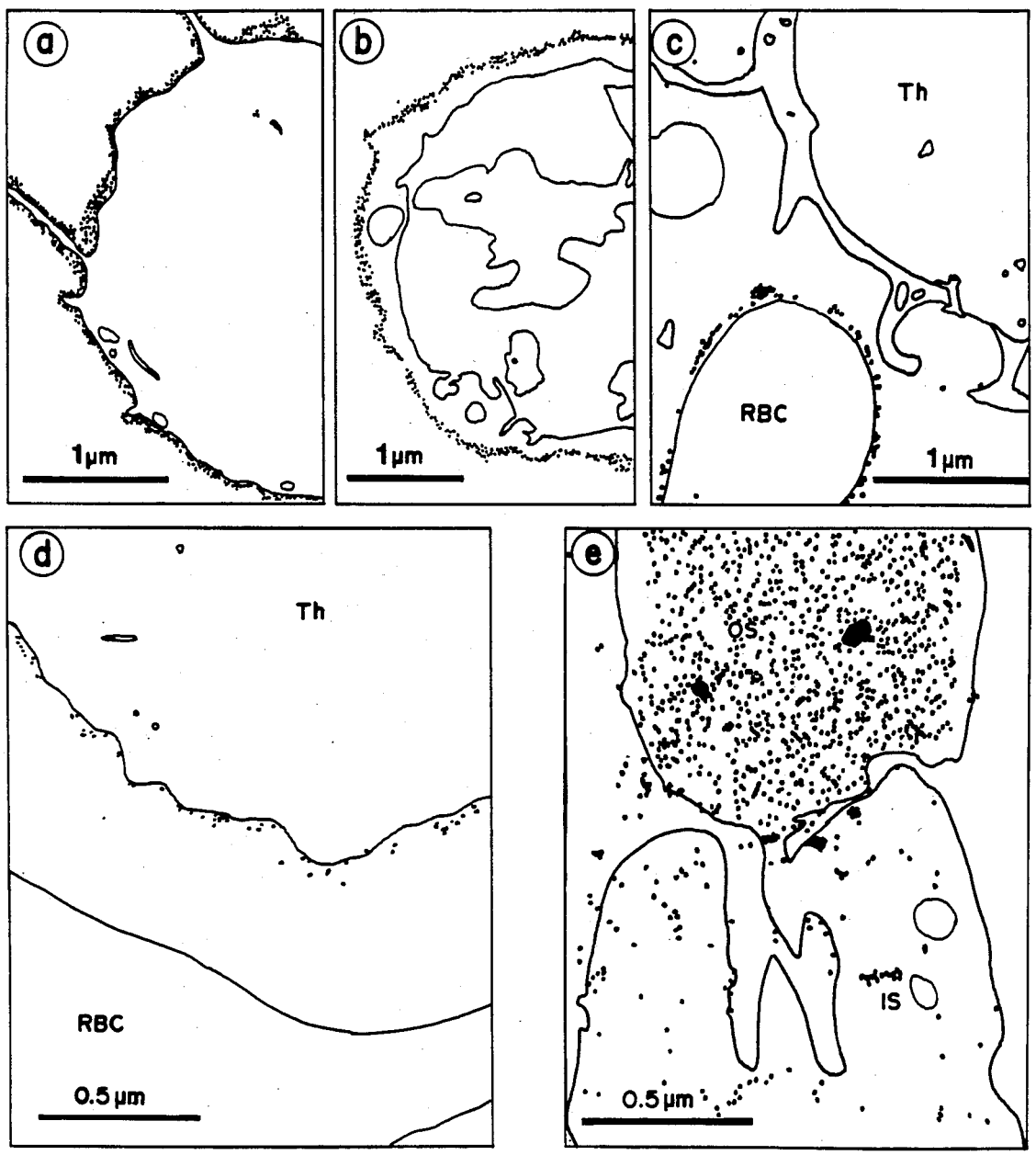
FIG. 2 (a) Pre-fixed rat thymocyte incubated with biotinylated RCA, 1 hr at 4 C, followed by avidin-DE-Au-Dex (approx 20 nm diameter), 1 hr at 4 C. (b) Pre-fixed rat thymocyte incubated with Con A, 1 hr at 4 C, followed by avidin-DE-Au-Dex (approx. 20 nm diameter), 1 hr at 4 C. (c) Pre-fixed rat thymocyte (Th) and red blood cell (RBC) incubated with WGA-DE-Au-Dex (approx. 40 nm diameter). Notice difference in labelling of two cell types. (d) Unfixed rat thymocyte (Th) and red blood cell (RBC) incubated with OX 7 (anti-Thy-1-antibody) 1 hr at 4 C; fixed in 0.2% glutaraldehyde, labelled with goat anti-mouse Ig-DE-Au-Dex (approx. 20 nm diameter), 1hr at 4 C. Only the thymocyte is labelled. (e) Glutaraldehyde-fixed, unosmicated bovine retina embedded in glycol methacrylate. Ultrathin sections of rod photoreceptor cell incubated with 1D4 (antirhodopsin antibody), 3 hrs at 4 C, followed by goat anti mouse Ig-DE-Au-Dex (approx. 25 nm diameter), 2 hrs at 4 C and contrasted with 1% Vanadatomolybdate, 30 mins at 22 C. Notice much heavier labelling of outer segment (OS) compared to inner segment (IS).

Application of Au-DE-Dex markers in the direct and indirect labelling of lectin receptors on thymocytes and red blood cells is shown in FIGS. 2a–c. Au-DE-Dex WGA conjugates did not label glutaraldehyde-fixed rat thymocytes, but did label red blood cells. In contrast, ricin and Con A receptors on rat thymocytes were heavily labelled. In these examples (FIGS. 2a and 2b) labelling was achieved by indirect lectin methods using avidin-Au-DE-Dex markers.

FIGS. 2d and 2e illustrate the use of indirect immunological labelling with Au-DE-Dex markers. Indirect labelling of the Thy-1 antigen on rat thymocytes with a monoclonal antibody is shown in FIG. 2d. Unfixed cells were sequentially labelled ith mouse-anti-Thy-1 antibody (OX 7), followed by goat-antimouse Ig-Au-DE-Dex particles. Controls (not shown) in which the primary antibody was omitted showed no labelling. FIG. 2e illustrates a thin sectin of a photoreceptor cell from glycol methacrylate embedded bovine retina. This section was incubated with a monoclonal anti-rhodopsin antibody (Molday and MacKenzie, *J. Immunol. Meth.* (1982) 52, 353–367), which was then detected using a goat-anti-mouse Ig-Au-DE-Dex conjugate. A dense labelling pattern was apparent in the rod outer segments where rhodopsin is localized in disk membranes. Sparse labelling of the inner segment presumably represents newly synthesized rhodopsin in transit to the outer segment.

Figure 3:
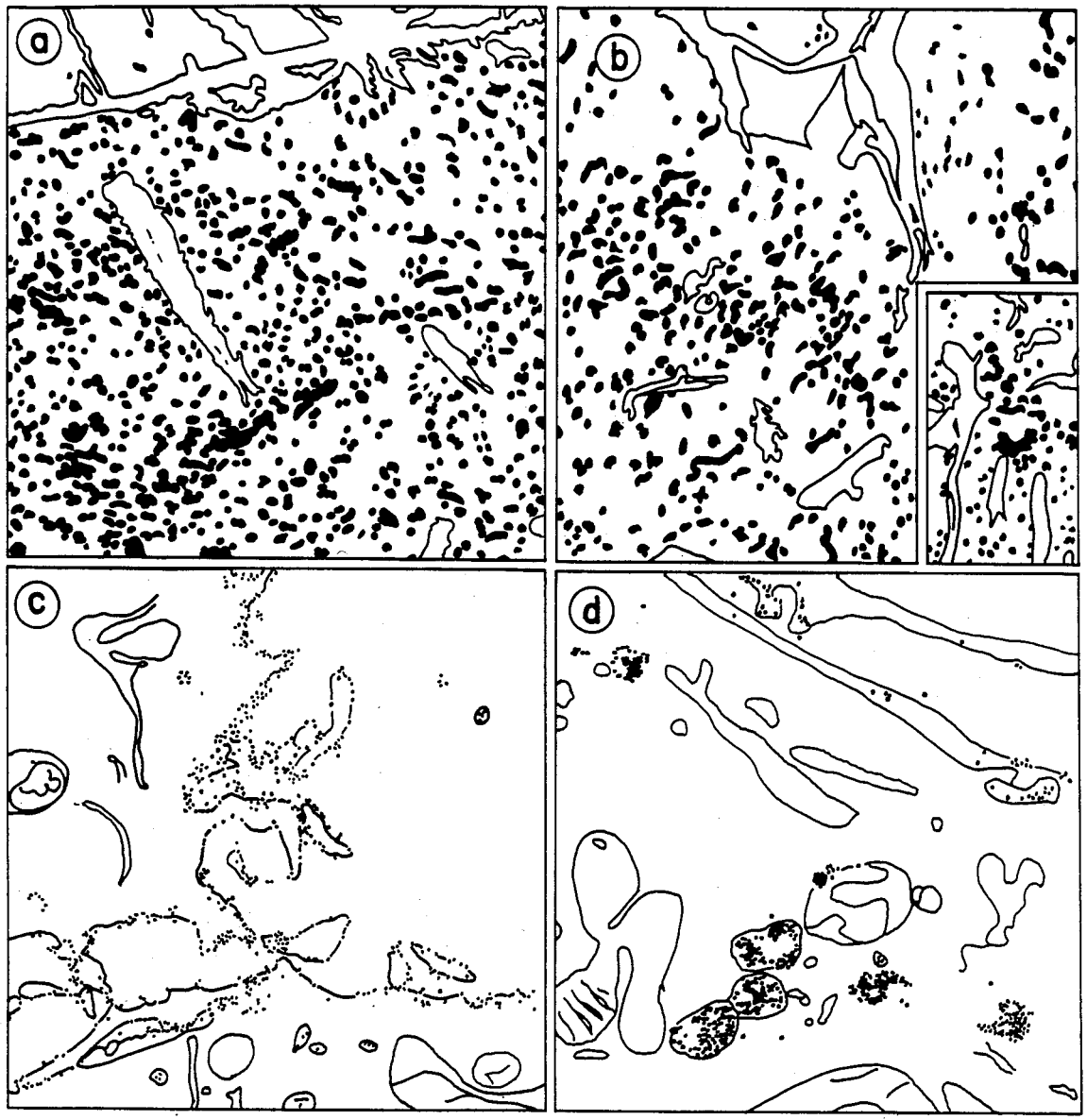
FIG. 3 Chinese hamster ovary cells labelled with WGA-DE-Au-Dex (approx. 20 nm diameter) conjugates. (a) Scanning electron micrograph and (b) transmission electron micrograph of a cell labelled at 4 C for 30 min. WGA-DE-Au-Dex (approx. 20 nm diameter) markers are randomly distributed over the cell surface. A few markers can be seen in vesicles within the cell. (c) Scanning electron micrograph and (d) transmission electron micrograph of a cell labelled at 4 C for 30 min., washed and subsequently incubated 25 C for 30 min. WGA-DE-Au-Dex (approx. 20 nm diameter) markers are only found on some regions of the cell. Holes on the cell surface can be seen often surrounded by markers. Markers can be seen either singularly or more often in aggregates in vesicles within the cell.

Correlative SEM-TEM studies on the distribution and internalization of WGA-binding sites on Chinese hamster ovary (CHO) cultured cells are shown in FIGS. 3a–d. When unfixed cells were labelled at 4 C.

for 30 minutes, most of the WGA-Au-DE-Dex markers were randomly distributed on the cell surface as visualized by SEM (FIG. 3a) and TEM (FIG. 3b). As the cells were warmed to 25 C. a decrease in the markers on the cell surface was observed with the appearance of highly regular holes on the cell surface (FIG. 3c). In some cases these holes were surrounded with WGA-Au-DE-Dex markers. At the TEM level, vesicles containing variable numbers of WGA-Au-DE-Dex markers could be seen within the cell and in some cases, lying in close proximity to lysomes (FIG. 3d).

Separation of Biologically Active Molecules

Different types of biologically active molecules can be separated by linking one type of such molecules in a mixture to particles as described, followed by separation based upon differing densities, for example by centrifuging. Alternatively, separation couls be accomplished based upon differences in size or charge between such linked and unlinked molecules.

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

I claim:

1. Colloidal sized particles each comprising a metal particle selected from the group consisting of gold, platinum and silver, coated with a derivative of a water-soluble compound which is polyethylene glycol or a water soluble polysaccharide having a molecular weight of between about 5,000 to 70,000, which derivative when not coating the metal particle has a plurality of pendant functional groups each containing a nitrogen atom which is positively charged in aqueous solution.

2. Colloidal sized particles each comprising a metal particle which exhibits a negative charge thereon in aqueous suspension, selected from the group consisting of gold, platinum and silver, coated with a derivative of a water-soluble compound selected from the group consisting of dextran, mannan, sucrose and polyethylene glycol, which derivative when not coating the metal particle has at least one pendant functional group which has a positive charge in aqueous solution and is a reaction product of said water-soluble compound and a compound selected from the group consisting of arginine, histidine and a diaminoalkane.

3. Particles as described in claim 2 wherein the water-soluble compound is dextran or mannan.

4. Particles as described in claim 2 wherein each particle is about 2 to 200 nm in size, and the water-soluble compound has a molecular weight of between about 5,000 and 70,000.

5. Particles as described in claim 1 wherein the derivative is a reaction product of the water soluble compound and a compound having two nitrogen atoms each of which has a positive charge in aqueous solution.

6. Particles are described in claim 5 wherein the compound having two nitrogen atoms is selected from the group consisting of arginine, histidine, and a diaminoalkane.

7. Particles as described in claim 6 wherein the polysaccharide is a polyhexose.

8. Particles as described in claim 7 wherein the polysaccharide is selected from the group consisting of dextran and mannan.

9. Particles as described in claim 1 wherein each particle is about 2 to 200 nm in size.

10. Colloidal sized particles of about 2 to 200 nm in size, each comprising a gold particle coated with the diaminoethane derivative of dextran with a molecular weight of 5,000 to 70,000.

11. A method of making colloidal sized particles comprising:
    (a) reacting a water soluble compound selected from the group consisting of dextran, mannan, sucrose and polyethylene glycol with a compound having two pendant functional groups each of which has a positive charge in aqueous solution and selected from the group consisting of arginine, histidine and a diaminoalkane, so as to produce a derivative of the water-soluble compound having a plurality of pendant functional groups each with a positive charge in aqueous solution;
    (b) coating an aqueous colloid of metal particles selected from the group consisting of gold, platinum and silver which exhibit a positive charge thereon, with the derivative.

12. A method as described in claim 11 additionally comprising oxidizing the water soluble compound prior to the reaction of step (a), and reacting the derivative of step (a) with a reducing agent so as to stabilize the derivative.

13. A method as described in claim 11 wherein the compound having two pendant functional groups is diaminoethane.

14. A method as described in claim 13 wherein the water soluble compound is selected from the group consisting of dextran and mannan.

15. A method as described in claim 13 wherein the water soluble compound is dextran.

16. A method of labelling biologically active molecules comprising linking them to colloidal sized particles each comprising a metal particle selected from the group consisting of gold, platinum and silver, coated with a derivative of a water soluble compound which is polyethylene glycol or a water soluble polysaccharide having a molecular weight of between about 5,000 to 70,000, which derivative when not coating the metal particle has a plurality of pendant functional groups each containing a nitrogen atom which is positively charged in aqueous solution.

17. A method as described in claim 16, wherein the derivative is a reaction product of the water soluble compound and a compound having two nitrogen atoms each of which has a positive charge in aqueous solution.

18. A method as described in claim 17, wherein the water soluble compound is dextran or mannan and the compound having two nitrogen atoms is selected from the group consisting of arginine, histidine and a diaminoalkane.

19. A method as described in claim 18, wherein the particles comprise gold particles coated with a diaminoethane derivative of dextran with a molecular weight of 5,000 to 70,000, said particles being about 2 to 200 nm in size.

20. A method of separating different types of biologically active molecules, comprising:
    (a) linking one type of biologically active molecules to particles each comprising a metal particle selected from the group consisting of gold, platinum and silver, coated with a derivative of a water soluble compound which is polyethylene glycol or a water soluble polysaccharide having a molecular weight of between about 5,000 to 70,000, which derivative when not coating the metal particle has a plurality of pendant functional groups each containing a nitrogen atom which is positively charged in aqueous solution;

(b) separating the linked molecules from step (a) from other biologically active molecules on the basis of differing densities.

21. A method as described in claim 20, wherein the water soluble compound is dextran or mannan and the derivative is a reaction product thereof with a compound selected from the group consisting of arginine, histidine and a diaminoalkane.

22. A method as described in claim 20, wherein the particles comprise gold particles coated with a diaminoethane derivative of dextran with a molecular weight of 5,000 to 70,000, said particles being about 2 to 200 nm in size.

* * * * *